US010004661B2

(12) United States Patent
Grant et al.

(10) Patent No.: US 10,004,661 B2
(45) Date of Patent: Jun. 26, 2018

(54) SYSTEM AND METHOD FOR TITRATING IN VIVO CELLULAR REACTION AND GENE EXPRESSION USING VARYING OSCILLATION FREQUENCIES

(71) Applicant: Strathspey Crown Holdings, LLC, Newport Beach, CA (US)

(72) Inventors: Robert Edward Grant, Laguna Beach, CA (US); Todd Mirzai, Honolulu, HI (US); Matthew T. Case, Laguna Hills, CA (US)

(73) Assignee: STRATHSPEY CROWN HOLDINGS, LLC, Newport Beach, CA (US)

( * ) Notice: Subject to any disclaimer, the term of this patent is extended or adjusted under 35 U.S.C. 154(b) by 0 days. days.

(21) Appl. No.: 15/862,110

(22) Filed: Jan. 4, 2018

(65) Prior Publication Data

US 2018/0125747 A1 May 10, 2018

Related U.S. Application Data

(63) Continuation of application No. 14/738,518, filed on Jun. 12, 2015, now Pat. No. 9,877,892, which is a continuation-in-part of application No. 14/488,101, filed on Sep. 16, 2014.

(51) Int. Cl.

| | |
|---|---|
| ***C12Q 1/68*** | (2018.01) |
| ***A61H 23/02*** | (2006.01) |

(52) U.S. Cl.

CPC . *A61H 23/0236* (2013.01); *A61H 2201/1623* (2013.01); *A61H 2201/5097* (2013.01); *A61H 2203/0456* (2013.01); *A61H 2205/081* (2013.01)

(58) Field of Classification Search

CPC ........ A61H 23/0236; A61H 2201/1623; A61H 2201/5097; A61H 220/081; A61H 2203/04565

See application file for complete search history.

(56) References Cited

U.S. PATENT DOCUMENTS

| | | | | |
|---|---|---|---|---|
| 6,024,690 | A | 2/2000 | Lee et al. | |
| 6,033,357 | A | 3/2000 | Ciezki et al. | |
| 6,077,213 | A | 3/2000 | Ciezki et al. | |
| 6,048,301 | A * | 4/2000 | Sabuda .................... | A61N 5/06 600/1 |
| 6,221,094 | B1 | 4/2001 | Bare | |
| 6,309,339 | B1 | 10/2001 | Ciezki et al. | |
| 6,626,816 | B1 | 9/2003 | Ciezki et al. | |
| 6,725,081 | B2 | 4/2004 | Ciezki et al. | |
| 7,280,874 | B2 | 10/2007 | Boehm | |
| 7,418,294 | B2 | 8/2008 | May | |
| 7,500,956 | B1 | 3/2009 | Wilk | |
| 8,326,408 | B2 | 12/2012 | Green et al. | |
| 8,440,154 | B2 | 5/2013 | Fahs, II et al. | |
| 8,591,419 | B2 | 11/2013 | Tyler | |

(Continued)

*Primary Examiner* — Glenn Richman

(74) *Attorney, Agent, or Firm* — Fish IP Law, LLP

(57) ABSTRACT

A system and method for the present invention utilizes a generator, in combination with a radiation unit, to direct waveform energy towards a target tissue using a predetermined protocol directed by titration-like feedback. The effect of the waveform energy on cellular structures of the target tissue is periodically monitored, and the predetermined protocol is halted when the cellular structure has been transformed into a desired phenotype.

21 Claims, 5 Drawing Sheets

(56) References Cited

U.S. PATENT DOCUMENTS

| | | | | |
|---|---|---|---|---|
| 2007/0128590 | A1* | 6/2007 | Boehm | C12N 13/00 435/6.12 |
| 2011/0004091 | A1* | 1/2011 | Brooks | A61B 5/0093 600/407 |
| 2011/0208113 | A1* | 8/2011 | Toma | A61K 35/44 604/22 |
| 2012/0130287 | A1* | 5/2012 | Gruber | A61N 7/00 601/2 |

* cited by examiner

SYSTEM AND METHOD FOR TITRATING IN VIVO CELLULAR REACTION AND GENE EXPRESSION USING VARYING OSCILLATION FREQUENCIES

This application is a continuation of U.S. patent application Ser. No. 14/738,518, filed Jun. 12, 2015, which is a continuation-in-part of U.S. patent application Ser. No. 14/488,101 filed Sep. 16, 2014, which is currently pending. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The present invention pertains generally to systems and methods which are used for conducting radiation therapy. More particularly, the present invention pertains to epidermal and/or implantable patches that generate and radiate energy toward target tissue inside the body of a person for therapeutic purposes. The present invention is particularly, but not exclusively, useful for incorporation into systems and methods that are used for electromagnetic or sonic radiation therapy and that include a titration capability for monitoring in vivo cellular and gene expression responses to the sonic radiation.

BACKGROUND

The following description includes information that may be useful in understanding the present invention. It is not an admission that any of the information provided herein is prior art or relevant to the presently claimed invention, or that any publication specifically or implicitly referenced is prior art.

It is well known that human beings will physically react to sonic energy. Hearing is but one example of this phenomenon. It often happens, however, that the human reaction to sonic energy is not immediately perceptible. Instead, the perception is the result of a longer term evolutionary process. In this last category, in vivo cellular reactions and gene expressions have been attributed to the influence of sonic radiation. Of particular interest here are cellular reactions that result in a phenotypic differentiation of the target tissue.

Apart from the phenotypic cell differentiation that can result from exposure to sonic radiation, it is also known that meditative states and/or alpha brain wave/relaxation states are greatly influenced by sonic radiation. On this point, consider the effect music can have on an individual. Also, consider the effect an exposure to loud, abrasive and/or startling noises can have on an individual, regardless whether the sound is instantaneous, repetitive or continuous.

Although a wide variety of protocols for sonic radiation therapy have 5 been, and can be, proposed, it is axiomatic that for beneficial therapy, sonic radiation must be effectively directed onto the proper target tissue. With this objective in mind, an effective delivery of sonic radiation necessarily requires a controlled exposure to the radiation. This control, in turn, requires the employment of preplanned operational parameters for the radiation (i.e. frequency, intensity, and duration), at predetermined exposure intervals. Preferably, all this is done with minimal requirements for patient supervision.

With the above in mind, it is an object of the present invention to provide a system and method for directing vibrational oscillating sonic waves toward a target tissue in the body of a person to influence a phenotypic differentiation of the target tissue at a cellular level. Another object of the present invention is to provide a system and method for using sonic radiation to induce meditative states and/or to establish alpha brain wave/relaxation states for the user. Yet another object of the present invention is to provide a system and method for monitoring the efficacy of sonic radiation therapy by employing a titration capability in the operational protocol. Still another object of the present invention is to provide a system and method for providing sonic radiation therapy that is easy to use, is simple to implement, and is relatively cost effective.

SUMMARY OF THE INVENTION

The present invention pertains generally to the transformational or morphological change of cellular tissue under the influence of waveform energy radiation. From an engineering perspective, it is well known that waveform energy radiation creates forces (i.e. exerts pressure) on an object when the radiation is incident on the object. Further, it is also well known that these external forces can cause changes to tissue structure. The present invention is based on this interactive phenomenon.

For purposes of the present invention, the target tissue of interest may be any in vivo or in vitro cellular structure of the human body. It may be an individual cell, or it may be a group of cells together within the intercellular tissue (matrix) that supports the cells. As envisioned for the present invention, target tissue may also be an identifiable structure inside a cell, such as a chromosome. In each case, it is important to appreciate that as a mechanical structure, the cellular structure of a target tissue will have a unique natural frequency.

An initial consideration for implementation of the present invention is the task of defining a desired phenotype for the outcome. For example, the objective of a protocol for the present invention may be the creation of a particular type of stem cell (e.g. liver cell) from an otherwise undefined or undifferentiated cell. In this case, the desired phenotype (outcome) will be defined to have the requisite characteristics of the particular type stem cell that is desired (e.g. liver cell). As another example, the objective of a protocol may be to terminate the viability of a cellular structure, such as by killing 3 cancer cells. Other examples can be cited. In each instance, however, and regardless of the specific outcome that is desired, the present invention employs waveform energy radiation for the purpose of epigenetically influencing a target tissue for its transformation or morphological change into a structure that corresponds to the desired phenotype.

As envisioned for the present invention, the radiation to be employed for influencing target tissue may be of any waveform energy known in the art It may be electromagnetic radiation in the spectrum between wavelengths of $10^{-25}$ m to $10^{3}$ m. It may also be periodic mechanical vibrations. In this latter case, the radiation may be acoustic sound waves in the range between 20 Hz and 20 kHz, and may also include infrasound waves (<20 Hz) and ultrasound waves (>20 kHz). Further, the radiation may be either continuous or pulsed, and the tone of the radiation may be either pure (single frequency) or complex (multi-frequency).

Structurally, a system for using a radiation of waveform energy to influence cellular structures within a target tissue will include a combination of various components. These include: components for generating and directing the radiation onto the target tissue; components for monitoring the target tissue; and a computer for controlling the generator and the radiation unit in accordance with a predetermined protocol.

In detail, the generator is used for generating the particular waveform energy radiation that is necessary to influence the target tissue. For this purpose it is important that the radiation be characterized by operational parameters having respective values which are established relative to the natural frequency of the target tissue. At a minimum, these operational parameters will include a frequency f and a volume intensity level v for the radiation, as well as a time duration $t_d$ during which the target tissue is to be radiated. A radiation unit, which is incorporated with the generator, may include optics that are used for directing the radiation electromagnetic radiation (e.g. lasers) onto the target tissue and the cellular structure. Specifically, all of this is done in accordance with a predetermined protocol that is designed to epigenetically influence the target tissue and the cellular 4 structure that may be within the target tissue. In a preferred embodiment of the present invention the radiation unit will be positioned at a distance d from the target tissue. Typically, the distance d will be greater than 10 millimeters (d>10 mm).

As indicated above, control over the system during the conduct of a protocol is managed by a computer. To do this, a device is provided for monitoring a phenotypic response of the target tissue and the cellular structure during the protocol. As envisioned for the present invention, this monitoring function can be performed by an appropriate sensor, or by the periodic performance of a biopsy. In the event, management and control of the protocol by the computer is terminated when the phenotypic response corresponds with the desired phenotype.

A method in accordance with the present invention begins by identifying the target tissue to be influenced (including the cellular structure), and by defining a desired phenotype for the target tissue. A natural frequency for the phenotype can then be determined by reference to the literature. It is then necessary to establish values for the operational parameters (e.g. p, v and $t_d$) that will properly characterize the radiation that is to be used. In particular, it is desirable to establish operational values that are operationally relative to the natural frequency of the target tissue (cellular structure). In detail, with knowledge of this natural frequency, the radiation frequency f can be set to resonate, or partially resonate, with the cellular structure that is to be influenced during conduct of the protocol.

Operationally, once parameters have been established for the radiation, the radiation can be directed onto the target tissue in accordance with a predetermined protocol. As noted above, the purpose here is to epigenetically influence the target tissue and the cellular structure. During the protocol, the target tissue is then monitored in a titration-like process to detect a phenotypic response from the target tissue and the cellular structure. The protocol is terminated when the phenotypic response corresponds with the desired phenotype.

In an embodiment of the present invention the radiation can be pulsed. For this embodiment, each radiation pulse will have a predetermined time duration $t_d$ within a predetermined time interval $t_i$. Specifically, ti will extend between the successive beginnings of respective radiation pulses (i.e. $t_i > t_d$).

In some embodiments of the inventive concept a system is provided for directing sonic waves toward preselected target tissue within the body of a person. This can be done for any of several reasons. For one, the sonic waves can be directed toward tissue to improve the overall health and wellness of the person. For another, they can be used to induce meditative states and/or to establish alpha brain wave/relaxation states for the person.

As envisioned, the system will include a patch that is attached to the human body. Thus, it may be either an epidermal patch or an implantable patch. In either case, and regardless where it is positioned on the user, the overall functionality of the patch is to direct sonic waves toward target tissue of the user in a manner that will entrain cellular functions locally in the target tissue, for an intended purpose.

Structurally, for a monopolar version of a system for the present invention, the patch will include a base member and a sonic generator which is mounted on the base member. In the case of an epidermal patch, a connecter is also included which may be either a fastener or an adhesive. For its use, the connector is affixed to the base member to hold the patch at a preselected location (position) on the body of the person (user).

A sounding board (speaker cone) can be employed with a sonic generator on the base member of the patch. If used, the sounding board speaker cone) will concentrate and more accurately direct operationally effective sonic frequencies toward the target tissue. Further, a transceiver can be mounted on the base member of the patch to establish a communication link between the sonic generator and a remote central control unit. In particular, the information to be transmitted by the transceiver from the patch to the central control unit will typically pertain to information that is pertinent to the operation of the sonic generator.

An extracorporeal titration unit is incorporated into the present invention to provide for communication between the patch and the central control unit. Specifically, the titration unit is employed to monitor the influence that the sonic waves have on the target tissue. In detail, the titration unit monitors changes of an expression level of the target tissue that result due to phenotypic differentiation of the tissue's cellular structure. This monitoring by the titration unit can be accomplished in either of several ways. For example, it can be accomplished using any of various imaging technologies, such as Optical Coherence Tomography (OCT) and ultrasound. The monitoring can also be accomplished by periodically conducting biopsies of the target tissue, or by taking periodic bio-impedance measurements.

For a bipolar version of the present invention, a second patch can also be employed in combination with the monopolar patch disclosed above. Like the patch for the monopolar embodiment disclosed above, this second patch may be either an epidermal or an implantable patch. Similarly, it can also be used anywhere on the body of the user. When used, the second patch will typically be complementary to the operation of the other patch. For instance, the second patch can be positioned on the opposite side of the body from the first patch to enhance bio-impedance measurements. It can also be used to radiate sonic energy simultaneously with the first patch to achieve different radiation perspectives on the target tissue.

Operationally, the system of the present invention can be employed to generate sonic waves in accordance with a scheduled program. As envisioned for the present invention, this program can provide for variations in the intensity and/or magnitude of oscillating frequencies of the sonic wave. Preferably, each frequency that is to be used will be selected from a sonic spectrum that includes ultrasonic, audible sonic, and infrasonic frequencies.

As implied above, the functionality of the present invention is established to achieve an intended outcome for the target tissue. In particular, this outcome will most likely be a phenotypic response for the target tissue. To achieve this, the titration unit monitors the target tissue during employment of the patch (system). Signals that are pertinent to the expression level (phenotypic differentiation) of the target tissue are then sent from the monitor to the central control unit. At the central control unit they are methodically compared with a desired phenotype (i.e. a base reference). Based on this comparison, employment of the system may be either continued or terminated. In particular, a use of the system for the present invention is to be terminated whenever the desired phenotype response has been achieved.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Figure 1:
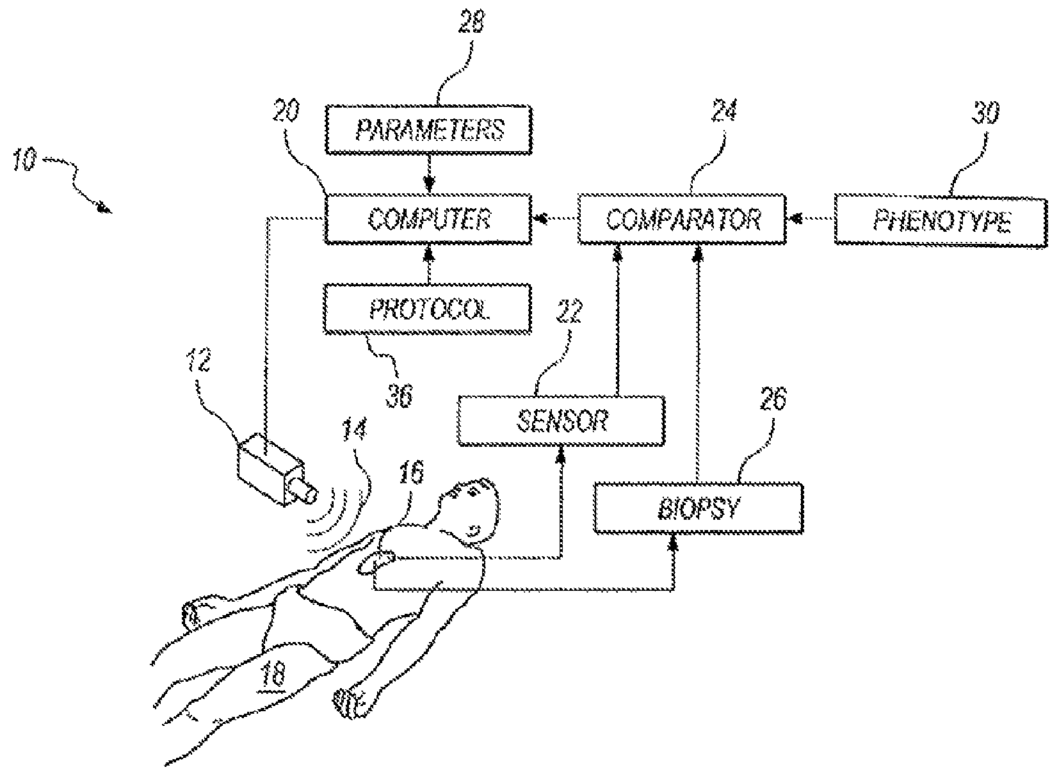
FIG. 1 is a schematic presentation of components for a system in accordance with the present invention.

Referring initially to FIG. 1 a system in accordance with the present invention is shown and is generally designated 10. As shown, the system 10 is to be used for radiating waveform energy to epigenetically influence cellular structures within a target tissue. To do this, the system 10 includes a unit 12 for directing radiation 14 toward a target tissue 16 of a patient 18. In particular, it is envisioned that the unit 12 will be capable of generating a waveform energy radiation 14 that spans the electromagnetic spectrum of wavelengths between $10^{-25}$ m and $10^{3}$ m. Further, it is envisioned that the 6 radiation 14 may also include acoustic sound waves in the range between 20 Hz and 20 kHz, as well as infrasound waves (<20 Hz) and ultrasound waves (>20 kHz). In the case of sound waves, the energy waveform of radiation 14 may be either a pure frequency or a complex frequency and, in the case of electromagnetic waves, the radiation 14 may have either a single wavelength f . . . , or a combination of different wavelengths. Also, as envisioned for the present invention, the target tissue 16 may be either in vivo as shown in FIG. 1, or it may be in vitro.

Still referring to FIG. 1, it will be seen that the system 10 includes a computer 20 which is connected with the unit 12. Depending on the particular application for system 10, the computer 20 may perform various functions during a same protocol. For instance, in addition to providing operational details for the radiation 14, the computer 20 may also be used to operationally control movements of the unit 12.

As also shown in FIG. 1, the system 10 also includes a sensor 22 which is used to monitor the target tissue 16, and to transfer information pertaining to the target tissue 16 to a comparator 24. For this purpose, the sensor 22 can be of any type well known in the pertinent art that is capable of epigenetically monitoring a transformation or morphology of the target tissue 16.

For example, sensor 22 may be employed to perform titration-like methodologies with processes such as bioelectrical impedance analysis and quantitative Polymerase Chain Reaction (PCR) techniques. The results of the monitoring performed by sensor 22 are then provided as input to the comparator 24. In the system 10, the comparator 24 is connected with the computer 20.

For an alternative to the use of a sensor 22 as disclosed above, it will be understood and appreciated by the skilled artisan that an epigenetic change (transformation/morphology) in the target tissue 16 can also be monitored by performing periodic biopsies 26 of the target tissue 16. Again, a titration methodology can be employed. In the event, the particular protocol which is used, its periodicity, and the extent to which the biopsy(ies) 26 is/are employed will be established on a case-by-case basis by the user of the system 10.

In addition to the hardware components for the system 10 mentioned above, various inputs for these components are required for an operation of the system 10. Importantly, the parameters 28 that are required for establishing the waveform energy of radiation 14 are a primary consideration. In particular the parameters 28 will necessarily include a selected frequency f for the vibration of the sound wave in the radiation 14. Also included will be the intensity level v for the max peak amplitudes of the sound wave, and a predetermined time duration $t_d$ for the radiation 14. Depending on the particular application, the time duration $t_d$ for the radiation 14 may be either continuous or pulsed.

Figure 2:
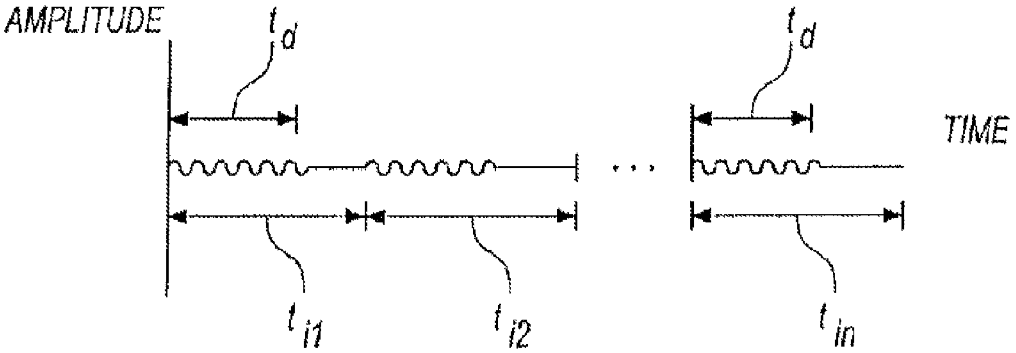
FIG. 2 is a time line of radiation pulses in a representative pulse train of waveform energy radiation in accordance with the present invention.

Referring to FIG. 2, time considerations for the radiation 14 are shown. If the radiation 14 is to be pulsed during an operation of the system 10, each radiation pulse will continue for a predetermined time duration $t_d$ within a predetermined time interval $t_i$. For a train of pulses (e.g. an n number of pulses as shown in FIG. 2), the predetermined time interval $t_i$; for each individual pulse can be established to extend between the successive beginnings of respective radiation pulses in the train (i.e. $t_i > t_d$). Stated differently, each pulse will have a length l; ($t_i$=time interval), during which the radiation 14 will be generated for the time duration td. On the other hand, for a continuous radiation 14, $t_d$ will equal 1; (i.e. $t_d = t_i$; and n=1).

Insofar as the frequency f of the radiation 14 is concerned, several considerations are possible. For one, as noted above, the frequency f may be pure or complex. For another, during a radiation 14, the predetermined frequency f may be alternated between a first frequency $f_1$ and a different second frequency $f_2$ (i.e. $f_1 \neq f_2$). Further, alternation of the frequencies may be set to occur at a predetermined repetition rate.

In an operation of the present invention, it is necessary for there to first 30 be a determination and an identification of a desired phenotype 30. By definition, as used for the present invention, a phenotype 30 is set of observable characteristics of an individual resulting from its interaction with 8 the environment. Here, reference to the word “individual” in the definition is taken to mean a cellular structure, a contiguous group of cellular structures, or a portion of a cellular structure, such as a chromosome. For the present invention, the cellular structure is alive and can be either in vivo or in vitro. With this in mind, consider the exemplary cellular structures 32 and 34 shown in FIG. 3.

Figure 3:
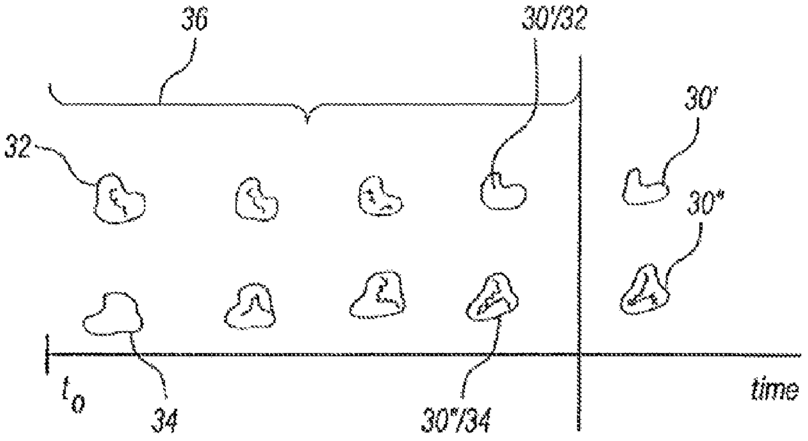
FIG. 3 is an illustration of the sequential progression of epigenetic influence on two different cellular structures during the transformation of the respective cellular structure into a desired phenotype.

For the examples presented here with reference to FIG. 3, consider the cellular structure 32 to be a cancer cell, and the cellular structure 34 to be an undifferentiated cell. The consequence on these respective cellular structures will then depend on the particulars of the protocol 36 that is employed for influencing a particular target tissue 16 with a particular radiation 14. Consider first, the transformation/morphology desired for an active cancer cell (cellular structure) 32. In this instance, the desired phenotype 30' will be a cancer-free cellular structure. Importantly, once the desired phenotype 30' has been identified, and defined, its definitional parameters 28 (including its natural frequency) must be input into the comparator 24. Depending on the characteristics of the desired phenotype 30', operational parameters 28 for the radiation 14 (i.e. f, $f_2$, $t_d$, n and $t_i$) are established. Specifics of the particular protocol 36 that are required to influence cellular structure 32 into the desired phenotype 30' are then followed and monitored.

In detail, during the conduct of a protocol 36, the sensor 22 (biopsy 26) is used to observe the cellular structure 32, and the comparator 24 is used to compare the cellular structure 32 with the desired phenotype 30'. Thus, the comparator 24 effectively monitors the transformation/morphology of the 25 cellular structure 32 as it is being influenced by the radiation 14. When the comparator 24 determines a cellular structure 30'/32 has been created which corresponds with the desired phenotype 30' (i.e. a cancer-free cell), the protocol 36 can be terminated.

For another example, consider the transformation/morphology of a cellular structure such as an undifferentiated cell 34. In this case, the desired phenotype 30" may be selected from any of various particular type cells (e.g. a liver cell). As with the earlier example, definitional parameters 28 for a 9 desired phenotype 30" are input into the comparator 24. Also, the required parameters 28 for radiation 14 are established, and an appropriate protocol 36 is followed. As before, when the comparator 24 determines a cellular structure 30"/34 has been created which corresponds with the desired phenotype 30" (i.e. a liver cell), the protocol 36 can be terminated.

Figure 4:
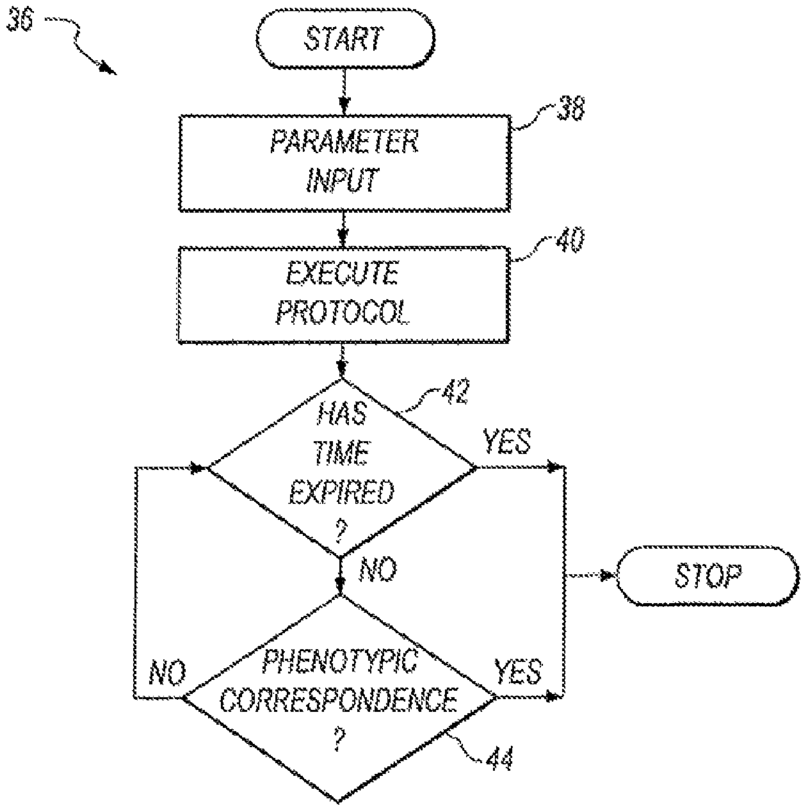
FIG. 4 is a flow chart of the interactive tasks involved in the methodology of the present invention.

For the conduct of a typical protocol 36, refer to FIG. 4. There it will be seen that block 38 requires parameter input for an operation of the system 10. Based on the above disclosure, it will be appreciated that this parameter input is really a two-step process. First, a desired phenotype (e.g. phenotype 30' or 30") needs to be identified and defined. Importantly, this includes selecting a natural frequency for the desired phenotype 30' or 30". Most often this can be accomplished by selecting a natural frequency from previously compiled empirical data. Second, the parameters 28 for operating the radiation unit 12 need to be established (i.e. f, v, td, n and ti).

Once system 10 has been set for operation as described above, block 40 indicates that the protocol 36 can be performed. The actual conduct of the protocol 36, however, is very event-dependent and may vary considerably depending on the transformation/morphology desired for a particular target tissue 16. Moreover, due to the titration-like methodology that is envisioned 20 by the present invention for a protocol 36, and the many variables that are involved, the actual conduct of a protocol 36 must necessarily be essentially under the purview of the user of the system 10. Accordingly, any time requirements for the protocol 36 that are to be maintained (see inquiry block 42), and a determination of phenotypic correspondence that is indicative of 25 operational completion (see inquiry block 44), are effectively dependent on operational judgments of the user.

Figure 5:
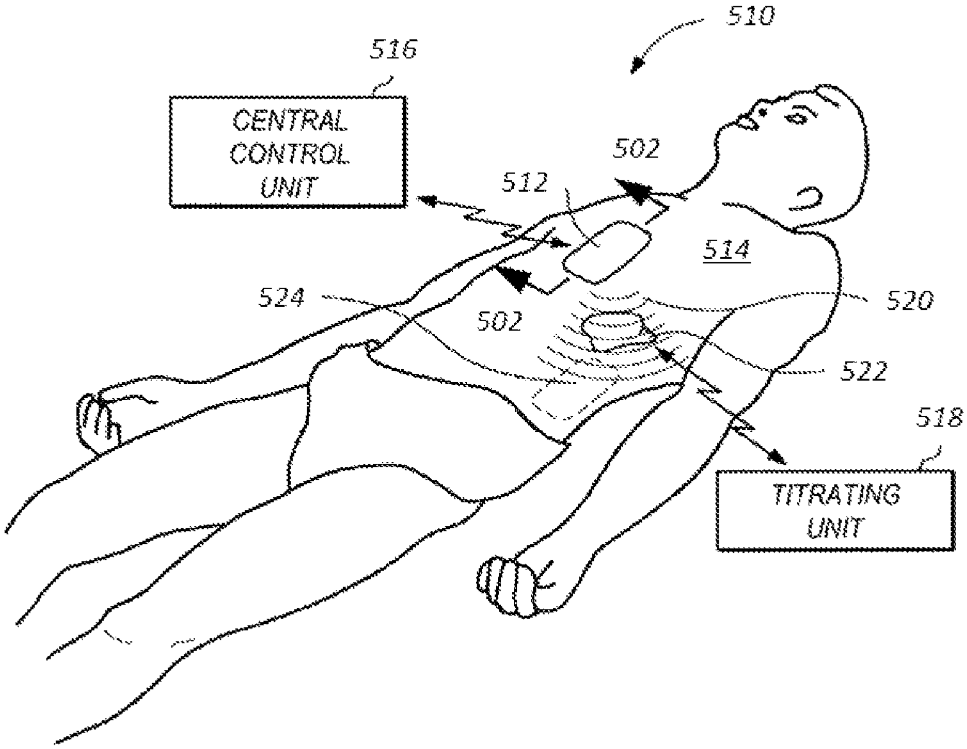
FIG. 5 is a perspective view of an epidermal patch in accordance with the present invention, shown in location on the body of a user, together with associated system operating components.

Referring initially to FIG. 5 a system for titrating in vivo cellular and gene expression therapies using varying oscillation frequencies is shown, and is generally designated 510. As shown, the system 510 includes a patch 512 that is somehow mounted on the body of a patient/user 514. For purposes of the present invention, the patch 512 may be either epidermal or implantable. FIG. 5 also shows that the system 510 includes a central control unit 516 and a titrating unit 518. As envisioned for the present invention, the central control unit 516 will typically be extracorporeal and will be connected in a wireless communication with the patch 512. As also envisioned for the present invention, the titrating unit 518 will be extracorporeal and can be any type of monitoring unit known in the pertinent art that is capable of accomplishing the intended purpose(s) of the present invention, such as an Optical Coherence Tomography (OCT) unit or an ultrasound unit.

Still referring to FIG. 5, it will be appreciated that the intended purpose for the patch 512 is to direct sonic radiation 520 onto target tissue 522 inside the body of the patient/user 514. FIG. 5 also shows that for a bipolar embodiment of the present invention, a second patch 524 can be incorporated into the system 510. In general, the second patch 524 will be substantially the same as patch 512. Accordingly, the disclosure below pertains to patch 524 as well as patch 512.

Figure 6:
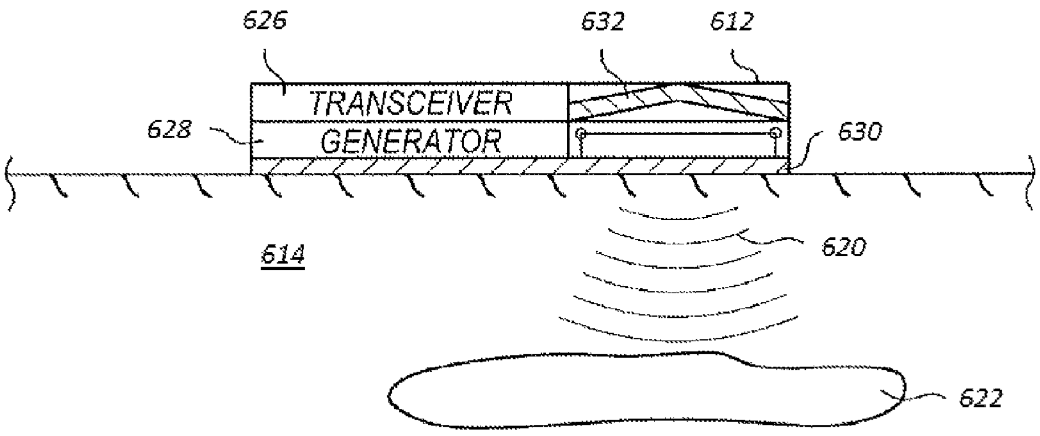
FIG. 6 is a cross-section view of the epidermal patch shown in FIG. 5.

In FIG. 6 it will be seen that the patch 612 itself can include a transceiver 526, a generator 628, an adhesive 630 and a sounding board (speaker cone) 632. In this combination, the transceiver 626 is provided to establish communication with the central control unit 516; the generator 628 is provided to give transmitting power to the sounding board (speaker cone) 532; and the adhesive 630 is provided as a means for attaching the patch 612/624 to the body of the patient/user 614.

For an operation of the present invention, a protocol is selected for the particular purpose of the intended operation of system 510. Essentially, this requires establishing operational parameters for the electromagnetic or sonic radiation 520. In detail, the selection of a frequency or frequencies, the intensity of each frequency to be used, the establishment of timed radiation intervals, the type of radiation to be employed (i.e. pulsed or continuous), and time requirements for the protocol are all to be considered as operational parameters. Furthermore, possible variations in any of these parameters during the course 520 of a protocol are also to be considered. As envisioned for the present invention, a selected protocol can be entered or pre-programmed in the central control unit 16. The protocol is then transmitted to the transceiver 26 of the patch 512/524, and the generator 28 is activated to operate the sounding board (speaker cone) 32 for directing radiation 520 (for example, sonic radiation) onto the target tissue 522.

It is also envisioned by the present invention that during the conduct of a protocol, the titrating unit 518 will be employed to monitor a phenotypic differentiation of the target tissue 522 at the cellular level. As disclosed above, this monitoring can be accomplished using OCT and/or ultrasound techniques. Additionally, it may be desirable to evaluate the target tissue 522 by periodically taking a biopsy of the target tissue 522.

An alternative protocol that may either complement phenotypic cell differentiation, or be conducted separately, is also envisioned for the present invention. In this case, the operational parameters set forth above can be selected to induce meditative states and/or to establish alpha brain wave/relaxation states for the patient/user 514. In all instances, regardless whether system 510 is used with a mono polar configuration (i.e. patch 512 only) or a bipolar configuration (i.e. both patch 512 and patch 24) the particular protocol to be followed is dependent on the needs of the patient/user 514.

While the particular System and Method for Titrating In Vivo Cellular Reaction and Gene Expression Using Varying Oscillation Frequencies as herein shown and disclosed in detail is fully capable of obtaining the objects and providing the advantages herein before stated, it is to be understood that it is merely illustrative of the presently preferred embodiments of the invention and that no limitations are intended to the details of construction or design 15 herein shown other than as described in the appended claims.

What is claimed is:

1. A system for directing a waveform energy toward a target tissue to modify a phenotypic differentiation of the target tissue at a cellular level, comprising:
- a waveform energy generator;
- a radiation unit that is in communication with the waveform energy generator and receives a waveform energy therefrom, wherein the radiation unit is positionable relative to the target tissue;
- a monitor that is configured to receive data related to the phenotypic differentiation of the target tissue; and;
- a controller that is in electronic communication with the monitor and at least one of the waveform energy generator and the radiation unit,
- wherein the controller comprises encoded instructions comprising both a predetermined treatment protocol and a logic operation comprising termination of the predetermined treatment protocol when data received from the monitor indicates the phenotypic differentiation of the target tissue corresponds to a desired phenotypic differentiation.

2. The system of claim 1, wherein the waveform energy is a sonic radiation having a wavelength ranging from 20 Hz to 20 kHz.

3. The system of claim 1, wherein the waveform energy is a sonic radiation having a wavelength of less than 20 Hz to 20 kHz.

4. The system of claim 1, wherein the waveform energy is a sonic radiation having a wavelength of greater than 20 kHz.

5. The system of claim 1, wherein the waveform energy is an electromagnetic energy having a wavelength of $10^{-25}$ m to $10^{3}$ m.

6. The system of claim 1, wherein the monitor receives data from a stepwise titration process.

7. The system of claim 6, wherein the stepwise titration process is selected from the group consisting of polymerase chain reaction and bioelectric impedance analysis.

8. A method of modifying a phenotypic differentiation of a target tissue at a cellular level, comprising:
- identifying the target tissue and a cellular structure of the target tissue;
- determining a natural frequency of the target tissue;
- determining a desired phenotype of the target tissue;
- providing a system comprising:
  - a waveform energy generator;
  - a radiation unit that is in communication with the waveform energy generator and receives a waveform energy therefrom, wherein the radiation unit is positionable relative to the target tissue;
  - a monitor that is configured to receive data related to the phenotypic differentiation of the target tissue; and;
  - a controller that is in electronic communication with the monitor and at least one of the waveform energy generator and the radiation unit,
  - wherein the controller comprises encoded instructions comprising both a predetermined treatment protocol and a logic operation comprising termination of the predetermined treatment protocol when data received from the monitor indicates the phenotypic differentiation of the target tissue corresponds to a desired phenotypic differentiation;
- positioning the radiation unit to direct the waveform energy towards the target tissue;
- emitting the waveform energy in accordance with the predetermined treatment protocol;
- using the monitor, collecting data related to the phenotypic differentiation of the target tissue and transmitting said data to the controller; and
- terminating emission of the waveform energy when the phenotypic differentiation of the target tissue correspond to the desired phenotypic differentiation.

9. The method of claim 8, wherein the predetermined protocol comprises the steps of:
- adjusting the waveform energy to a frequency f;
- adjusting the amplitude of the waveform energy to an intensity level v; and
- providing a time duration $t_d$, during which the waveform energy is emitted.

10. The method of claim 9, wherein emission of the waveform energy is continuous through time duration $t_d$.

11. The method of claim 9, wherein emission of the waveform energy is intermittent through time duration $t_d$.

12. The method of claim 9, wherein adjustment of the frequency f is accomplished by alternating between a first frequency $f_1$ and a second frequency $f_2$, wherein $f_1$ and $f_2$ are different frequencies.

13. The method of claim 12, wherein alternation between $f_1$ and $f_2$ is performed at a predetermined repetition rate.

14. The method of claim 9, wherein emission of the waveform energy is provided as a plurality of waveform energy pulses, wherein each one of the plurality of waveform energy pulses has a time duration $t_d$ and is separate from an adjacent one of the plurality of waveform energy pulses by a predetermined time interval $t_i$, and wherein $t_i$ is greater than $t_d$.

15. The method of claim 9, further comprising the steps of:
- positioning the radiation unit at a distance d from the target tissue; wherein d is greater than 10 mm; and
- using the radiation unit, focusing the waveform energy on the target tissue.

16. The method of claim 9, wherein the waveform energy is a sonic radiation having a wavelength ranging from 20 Hz to 20 kHz.

17. The method of claim 9, wherein the waveform energy is a sonic radiation having a wavelength of less than 20 Hz to 20 kHz.

18. The method of claim 9, wherein the waveform energy is a sonic radiation having a wavelength of greater than 20 kHz.

19. The method of claim 9, wherein the waveform energy is an electromagnetic energy having a wavelength of $10^{-25}$ m to $10^{3}$ m.

20. The method of claim 9, wherein the monitor receives data from a stepwise titration process.

21. The method of claim 9, wherein the stepwise titration process is selected from the group consisting of polymerase chain reaction and bioelectric impedance analysis.

* * * * *